United States Patent [19]

Jochum et al.

[11] Patent Number: 5,100,929
[45] Date of Patent: Mar. 31, 1992

[54] (POLYENE-POLYTHIOL) DENTAL COMPOSITIONS CURABLE WITH VISIBLE LIGHT

[75] Inventors: Peter Jochum; Oswald Gasser; Erich Wanek, all of Seefeld; Rainer Guggenberger, Hechendorf; Klaus Ellrich, Wörthsee, all of Fed. Rep. of Germany

[73] Assignee: Espe Stiftung & Co. Produktion-und Vertriebs KG, Fed. Rep. of Germany

[21] Appl. No.: 429,149

[22] Filed: Oct. 30, 1989

[30] Foreign Application Priority Data

Nov. 4, 1988 [DE] Fed. Rep. of Germany ....... 3837569

[51] Int. Cl.$^5$ .................. C08F 2/46; C08J 3/28; C08K 9/06; C08G 75/04
[52] U.S. Cl. ..................... 522/64; 522/180; 522/908; 523/109; 523/300
[58] Field of Search .......... 522/64, 180, 908; 523/109, 300

[56] References Cited

U.S. PATENT DOCUMENTS

| | | | |
|---|---|---|---|
| 3,066,112 | 11/1962 | Bowen | 260/41 |
| 3,661,744 | 5/1972 | Kehr et al. | 204/159 |
| 3,700,574 | 10/1972 | Kehr et al. | 522/64 |
| 3,729,404 | 4/1973 | Morgan | 204/159.15 |
| 3,825,518 | 7/1974 | Foster et al. | 260/42.52 |
| 3,862,920 | 1/1975 | Foster et al. | 260/42.52 |
| 4,119,617 | 10/1978 | Hanyuda et al. | 528/360 |
| 4,292,152 | 9/1981 | Lechtken et al. | 522/64 |
| 4,298,738 | 11/1981 | Lechtken et al. | 546/22 |
| 4,324,744 | 4/1982 | Lechtken et al. | 260/932 |
| 4,351,853 | 9/1982 | Jochum et al. | 427/2 |
| 4,385,109 | 5/1983 | Lechtken et al. | 430/306 |
| 4,435,497 | 3/1984 | Irving | 430/288 |
| 4,468,202 | 8/1984 | Cohen | 433/199 |
| 4,553,936 | 11/1985 | Wang | 433/37 |
| 4,591,522 | 5/1986 | Kang et al. | 428/419 |
| 4,668,713 | 5/1987 | Woods et al. | 522/174 |
| 4,710,523 | 12/1987 | Lechtken et al. | 522/14 |
| 4,737,593 | 4/1988 | Ellrich et al. | 568/15 |
| 4,761,136 | 8/1988 | Madhavan et al. | 433/214 |
| 4,813,875 | 3/1989 | Hare | 433/214 |

FOREIGN PATENT DOCUMENTS

| | | |
|---|---|---|
| 0173567 | 3/1986 | European Pat. Off. |
| 2816823 | 10/1978 | Fed. Rep. of Germany |
| 3141743 | 7/1982 | Fed. Rep. of Germany |
| 3316591 | 10/1984 | Fed. Rep. of Germany |
| 3532997 | 4/1986 | Fed. Rep. of Germany |
| 1225998 | 8/1985 | German Democratic Rep. |

Primary Examiner—Marion E. McCamish
Assistant Examiner—Susan Berman
Attorney, Agent, or Firm—Frost & Jacobs

[57] ABSTRACT

Photopolymerizable dental compositions are proposed which are curable with visible light and which apart from usual auxiliary substances and additives contain polymerizable monomers of the group of the poly-thiol compounds and of the group of the poly-ene compounds and a photoinitiator and which, in order to obtain a curing free from any smeary layer, contain at least 10% by weight poly-thiol compound(s), at least 10% by weight poly-ene compound(s) and 0.01 to 5% by weight of at least one acyl phosphine compound as photoinitiator. The compositions can advantageously be used as dental impression compositions.

15 Claims, No Drawings

(POLYENE-POLYTHIOL) DENTAL COMPOSITIONS CURABLE WITH VISIBLE LIGHT

The invention relates to photopolymerizable dental compositions which are curable with visible light and which apart from the usual auxiliary substances and additives contain polymerizable monomers of the group of the poly-thiol compounds each having at least two thiol groups and polymerizable monomers of the group of the poly-ene compounds each having at least two ethylenically unsaturated groups and at least one photoinitiator.

A number of photopolymerizable compositions are already known which can be cured with visible light, i.e. light with a wavelength in the range from 400 to 800 nm. Thus, EP-A-0 007 508 and 0 057 474 describe photopolymerizable compositions containing certain monoacyl phosphine oxides as photoinitiators. The compositions described therein can be cured with light >400 nm; however, small curing depths and curing rates, unsatisfactory storage stabilities and a pronounced smeary layer, caused by inhibition with atmospheric oxygen, are disadvantages which make handling of the compositions described therein difficult and restrict their possible uses.

DE-A 3,443,221 describes photopolymerizable preparations containing bisacyl phosphine oxides. These compositions, which are readily curable with visible light, admittedly have greater curing depths and curing rates as well as better storage stabilities than the aforementioned compositions but due to inhibition by atmospheric oxygen their surface is likewise coated with a disadvantageous smeary layer.

Photopolymerizable preparations on the basis polyene/polythiol are for example known from U.S. Pat. No. 3,661,744, DE-A-3,546,019 and EP-A-0 069 069. Apart from the poly-enes and the poly-thiols they contain UV initiators such as benzophenone. The preparations described therein are, however, not curable with visible light with a wavelength >400 nm.

U.S. Pat. No. 3,729,404 describes photocurable polyene/poly-thiol compositions to which certain phosphines are added as activators. The addition of phosphines produces an appreciable increase in the reaction rate. Curing with visible light is not described.

To avoid the smeary layer caused by oxygen inhibition in photopolymerizable compositions a whole series of counter measures have already been proposed: A summary will be found in the article by George F. Vesley "Mechanisms of the Photodecomposition of Initiators" in the Journal of Radiation Curing, January 1986, pages 9 and 10. Apart from the technically very complicated proposal of carrying out the curing under a protective gas atmosphere, as a rule it is proposed that high initiator concentrations be used or so-called "oxygen interceptors" be added to the polymerizable compositions. Suitable "oxygen interceptors" are, for example, tertiary amines and certain furans. This enables an appreciable reduction of the smeary layer to be achieved but only when curing with very high-energy light of small wavelength (<400 nm). It is further proposed to add surfactive photoinitiators with which at the surface a pronounced increase of the photoinitiator concentration and thus a reduction of the smeary layer can be achieved. However, all the steps described here have hitherto been possible only with UV initiators responding to light of a wavelength <400 nm and a complete avoiding of the smeary layer is not possible with these steps. Moreover, the increase in the photoinitiator concentration on further radiation, for example by sunlight, causes in the cured compositions an increased discolouration and destruction of the polymer matrix by photodegradation initiated by photoinitiator molecules which have not been used up.

So far, all the attempts to transfer the steps described above contributing to a reduction of the smeary layer in UV-curing compositions to the field of compositions which can be cured with visible light (>400 nm) were unsuccessful. For instance, with combinations of photoinitiators responsive to visible light, for example campher quinone and acyl phosphine oxides, with tertiary amines photopolymerizable compositions are obtained which, although they can be cured with visible light, after the curing due to oxygen inhibition have a pronounced layer of smear (cf. DE-A-3,443,221). For this reason, in the field of dental materials relatively complicated methods are employed to prevent the formation of smear. Thus, it has been proposed that the curing of dental veneer materials be carried out in a liquid bath (DE-A-3,316,591) or the curing effected under vacuum (DE-A-3,001,616).

The invention is therefore based on the problem of providing novel compositions which can be cured with visible light without formation of a smeary layer and can be used in particular as dental compositions.

This problem is solved by the preparation of the dental compositions according to the invention.

The subject of the invention is photopolymerizable dental compositions which are curable with visible light and which apart from the usual auxiliary substances and additives contain polymerizable monomers of the group of the poly-thiol compounds each having at least two thiol groups and polymerizable monomers of the group of the poly-ene compounds each having at least two ethylenically unsaturated groups and at least one photoinitiator, which are characterized in that the compositions contain respectively related to the sum of all the polymerizable monomers (a) at least 10% by weight of one or more of the polythiol compounds, (b) at least 10% by weight of one or more of the poly-ene compounds and (c) as photoinitiator 0.01–5% by weight of at least one acyl phosphine compound of the general formula I

wherein $m=1$, $n=1$ and $x=0$ (oxygen)

or $m=2$, $n=0$ and $x=0$ (oxygen) or S, $R^1$ is a straight-chain or branched $C_{1-6}$-alkyl radical, a cyclopentyl, cyclohexyl, phenyl, naphthyl or biphenylyl radical which is optionally substituted by F, Cl, Br, I, $C_1$–$C_{12}$-alkyl and/or $C_1$–$C_{11}$- alkoxyl, an S or N-containing 5 or 6-member heterocyclic ring;

$R^2$ and $R^3$, which are identical or different, denote a cyclohexyl, cyclopentyl, phenyl, naphthyl or biphenylyl radical, a cyclopentyl, cyclohexyl, phenyl, naphthyl or biphenylyl radical which is substituted by F, Cl, Br, I, $C_1$-$C_{12}$-alkyl and/or $C_1$-$C_{11}$-alkoxyl, or an S or N-containing 5 or 6-member heterocyclic ring or $R^2$ and $R^3$ are linked together to form a ring which contains 4 to 10 carbon atoms and can be substituted by 1 to 6 $C_{1-4}$-alkyl radicals.

In addition to the components (a) to (c) the dental compositions according to the invention may contain as component (d) 20-79.99% by weight, with respect to the total of all the polymerizable monomers, of an acrylic acid and/or methacrylic acid ester of an at least difunctional alcohol.

The subject of the invention is further the use of the dental compositions according to the invention as dental impression compositions.

The compositions according to the invention can be surprisingly cured without formation of a smeary layer with visible light of a wavelenght >400 nm. This makes is possible for the first time to combine the advantages of the curing with visible light, which include obtaining great curing depths even with highly pigmented systems, avoiding the inherent absorption of the polymer matrix and the possibility of irradiating even through substrates, for example through polycarbonate, PMMA and the like, with the advantage of obtaining surfaces which do not have a smeary layer without any particular apparatus expenditure such as vacuum, protective gas or liquid bath. Further advantages of the compositions according to the invention are the high storage stability, high curing rate, low yellowing tendency and low residual monomer content.

A great number of advantageous possible uses are thus open to the compositions according to the invention. Attention is drawn, for example, to coatings, embeddings, castings and bondings inside and outside dentistry and, generally speaking, the curing of all compounds in which after the curing free surfaces are accessible.

For example, the compounds according to the invention could be used to coat crown and bridge members made from metal with tooth-like coloured dental compounds curable with visible light. The previously necessary complicated working under vacuum or liquid is dispensed with. The properties of the compositions according to the invention can be utilized in particularly advantageous manner in taking impressions in the mouth of the patient. Apart from the hitherto known use of two-component compounds which must first be homogeneously mixed before taking the impression, hitherto only photocuring impression compounds on the basis of radically curing acrylate systems were known, cf. for example EP-A-0 170 219, 0 255 286. However, with these compounds, because of the inhibition by atmospheric oxygen, at all free and moist surfaces there is a danger of the formation of a permanent pronounced smeary layer which represents to the dentist an extreme contamination risk because these surfaces are also extremely tacky. Moreover, the impressions taken with these compositions are extremely difficult to cast for the dental technician because the composition can mix with the model material at the unpolymerized parts of the surface.

With the compositions according to the invention these disadvantages can be eliminated. The elastomeric properties necessary for making the impressions can be adjusted in the usual manner by appropriate selection of the poly-thiol and poly-ene components and of the fillers used.

The poly-thiols of the component (a) to be used according to the invention are preferably employed in an amount of at least 20% by weight with respect to polymerizable monomers. Preferably, at least one third of the poly-thiol compounds used is at least trifunctional, i.e. contains at least three thiol groups per molecule. Usable poly-thiol compounds are described in U.S. Pat. Nos. 3,661,744 and 4,119,617. The poly-thiol compounds preferably have a molecular weight in the range between 150 and 20,000; advantageously, the molecular weight is at least 500, particularly preferably at least 1,000.

For the use for making impression compositions curable by visible light without the formation of any smeary layer, advantageously poly-thiol compounds having a mean molecular weight of from 500 to 10,000, particularly preferably of from 1,000 to 7,000, are used.

As poly-thiol compounds, according to the invention compounds may be used which correspond to the general formula

$$R^0-(SH)_n,$$

wherein $R^0$ stands for an organic radical which is preferably free from ethylenically unsaturated double bonds, and n denotes an integer $\geq 2$, preferably 2, 3 or 4.

Well-suited poly-thiol compounds are, for example, polyoxyalkylene triols with mercaptan end groups. Examples of such compounds are the commercially available Capcure ® 3-800 having the general formula

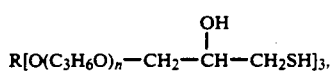
$$R[O(C_3H_6O)_n-CH_2-\underset{\underset{OH}{|}}{CH}-CH_2SH]_3,$$

wherein R denotes an aliphatic hydrocarbon radical having 1-12 C-atoms and n is an integer from 1 to 25, and Capcure ® 5-1300 having the following formula

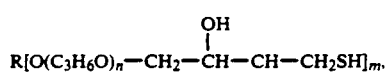
$$R[O(C_3H_6O)_n-CH_2-\underset{\underset{OH}{|}}{CH}-CH-CH_2SH]_m,$$

wherein R denotes an aliphatic hydrocarbon radical having 1-12 C-atoms, n is the number 1 or 2 and m the number 5 or 6.

For the use as impression compositions very suitable polythiol compounds are also the reaction products of mercaptocarboxylic acids with polyoxyalkylenes such as, for example, polyethylene oxides having at least two terminal hydroxy groups, polypropylene oxides or copolymers of ethylene oxide and propylene oxide each having at least two terminal hydroxy groups. Also particularly well-suited are copolymers of ethylene oxide with tetrahydrofuran. These aforementioned polyether-di or poly-ols preferably have a mean molecular weight of 500-10,000, and particularly preferably of 1,500-7,000.

Also well-suited are the esters of mercaptocarboxylic acids with at least trifunctional alcohols. Examples of this compound class are the mercaptocarboxylic acid esters of trimethylol propane and of pentaerythrite. The mercaptocarboxylic acids used here have carbon skeletons having 2 to 20 C-atoms, preferably 5 to 15 C-atoms. Well-suited are for example trimethylol propane tris-mercaptoundecanoate or pentaerythrite tetrakismercaptoundecanoate. Another poly-thiol which also is very suitable is trismercaptoethyl isocyanurate.

The poly-ene compounds to be used according to the invention are employed in an amount of at least 10% by weight with respect to polymerizable monomers, at least 20% by weight being preferred. In a particularly preferred embodiment poly-thiol and poly-ene compounds are used as only monomers so that together they make up 100% by weight of the polymerizable monomers.

The at least 2 ethylenically unsaturated groups ("ene groups") of the poly-ene compounds to be used according to the invention may possibly be substituted. Preferably, at least one third of the poly-ene compounds used contains at least 3 "ene groups" which may possibly be substituted. By definition, ene groups means for example: O-allyl, N-allyl, O-vinyl, N-vinyl and p-vinyl phenol ether groups. Possible poly-enes are described in U.S. Pat. No. 3,661,744 and EP-A-0 188 880. The poly-ene may for example have the following structure $(A)-(X)_m$.

wherein m is an integer $\geq 2$, preferably 2, 3 or 4, and X is selected from the group consisting of

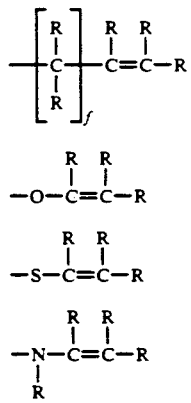

wherein f is an integer from 1 to 9 and the radical R can have the meanings H, F, Cl, furyl, thienyl, pyridyl, phenyl and substituted phenyl, benzyl and substituted benzyl, alkyl and substituted alkyl, alkoxy and substituted alkoxy as well as cycloalkyl and substituted cycloalkyl and in each case may be the same or different.

(A) is an at least difunctional organic radical which is made up of the atoms which are selected from the group consisting of C, O, N, Cl, Br, F, P, Si and H.

The poly-ene compounds preferably have mean molecular weights in the range of 64–20,000, preferably 200–10,000 and particularly preferably 500–5,000.

Well-suited poly-ene compounds are, for example, the allyl and/or vinyl esters of at least difunctional carboxylic acids. Suitable as carboxylic acids for this purpose are those with carbon chains of 2 to 20 C-atoms, preferably 5 to 15 C-atoms; also well-suited are allyl and vinyl esters of aromatic dicarboxylic acids such as phthalic acid or tri-mellitic acid. Examples which can be named are succinic acid diallyl ester and succinic acid divinyl ester, phthalic acid diallyl ester and phthalic acid divinyl ester.

Also well-suitable are allyl ethers of polyfunctional alcohols, for example polyether-di or poly-ols, such as polyethylene oxides, polypropylene oxides, their copolymers or also copolymers of ethylene oxide and tetrahydrofuran. Preferred are the allyl ethers of at least trifunctional alcohols. Examples which can be named are the allyl ethers of trimethylol propane, pentaerythrite triallyl ether acrylate or 2,2-bis-oxyphenyl propane-bis-(diallyl phosphate).

Also well-suited are compounds of the type cyanuric acid triallyl ester, triallyl triazine trione and the like.

In the case of the additional presence of component (d) it may be advantageous to use polyfunctional alcohols partially with allyl ether end groups and partially with acrylic acid ester or methacrylic acid ester end groups.

The molar ratio of poly-thiol to poly-ene to be used is to be chosen so that a complete polymerization is possible. The molar ratio of ene to thiol groups is normally from 0.2:1 to 5:1, preferably from 0.75:1 to 1.5:1.

Suitable as impression compositions are compositions in which at least one of the components (thiol or ene) has a polyether centre piece of the aforementioned type.

The acyl phosphine compounds to be used according to the invention are preferably employed in an amount of 0.1–3% by weight, particularly preferably from 0.2 to 1% by weight, in each case with respect to the polymerizable monomers.

Preferred acyl phosphine compounds of the general formula I are monoacyl phosphine oxides with 2,4,6-trimethylbenzoyl-diphenyl phosphine oxide being particularly preferred. Bisacyl phosphine oxides, for example bis-(2,6-dichlorobenzoyl)-4'-n-propylphenyl phosphine oxide, can also advantageously be used.

As mentioned, 20–79.99% by weight of the polymerizable monomers may consist of acrylic acid and/or methacrylic acid esters of at least difunctional alcohols. Preferably, 40–60% by weight is employed. As acrylic acid and/or methacrylic acid esters, monomeric and polymeric acrylates and methacrylates may be used. Well-suited, for example, are the long-chain monomers according to U.S. Pat. No. 3,066,112 on the basis of bisphenol-A and glycidyl methacrylate or their derivatives formed by addition of isocyanates; also suitable are the acrylic acid and methacrylic acid esters of mono or multivalent alcohols, for example methyl and ethyl methacrylate, in particular the esters of multivalent alcohols such as triethylene glycol di(meth)acrylate and trimethylol propane-tri(meth)acrylate. Also suitable are compounds of the type bisphenol A-bis-oxy-ethyl(meth-)acrylate and bisphenol A-bis-oxy-propyl(meth)acrylate.

Particularly suitable are the diacrylic and dimethacrylic acid esters of bis-hydroxy-methyl-tricyclo [5.2.1.0$^{2,6}$]-decane, as mentioned in DE-Patent No. 2,816,823. It is also possible to use the reaction products of diisocyanates and hydroxy-alkyl(meth)acrylates as described in DE-A-2,312,559. Of course, mixtures may also be used of monomers and/or unsaturated polymers made therefrom.

The dental compositions according to the invention may also contain the usual auxiliary substances and additives, for example fillers, thixotropy aids, colouring and aromatic substances and plasticizers or softeners. Suitable fillers are all the fillers usually employed in dentistry for compositions curable with visible light, such as finely ground glass, quartz glass, quartz, calcium carbonate and the like. The fillers preferably have a grain distribution in the range of from 0.001 to 50 μm, particularly preferably in the range of from 0.001 to 10 μm. Well-suited are finely divided silicic acids such as pyrogenic silicic acid or precipitated silicic acid which can act simultaneously as thixotropy aids. The fillers and thixotropy aids used are preferably silanized. As silanizing agents the silane coupling agents known per se can be employed, for example γ-methylacryloxypropyl trimethoxysilane. The amount of fillers can vary in a wide range depending on the field of use. It is up to 90% by weight with respect to the total composition; a range of 10-50% by weight is preferably employed.

As plasticizers all the plasticizers generally used in the chemistry of plastics and rubber can be employed. Well-suited are, for example, copolymers of ethylene and propylene oxide, dialkyl phthalates, for example dioctyl phthalate, dibenzyl toluene or acetyltributyl citrate. The amount of plasticizers also depends very much on the intended use. For dental impression compositions a concentration range of 0-20% by weight, preferably 0-5% by weight, has been found particularly advantageous.

The invention will be further explained hereinafter by reference to the following examples:

EXAMPLE 1:

(a) 50 parts by weight pentaerythrite tetramercaptoproprionate,
(b) 50 parts by weight triallyl triazine trione and
(c) 0.5 parts by weight 2,4,6-trimethylbenzoyl diphenyl phosphine oxide are mixed with 0.1 parts by weight pyrocatechol (inhibitor for preventing premature polymerization) to give a homogeneous solution.

The transparent solution thus obtained is introduced into a cylindrical mould of polyoxymethylene (diameter 5 mm, length 40 mm). The composition is exposed through the open end side of the cylindrical mould for 20 seconds with visible light of a wavelength of >400 nm by means of a commercially available dental radiator (Elipar-Visio/ESPE). To determine the curing depth or the thickness of the cured layer the soft or gel-like components not polymerized remote from the irradiated surface are removed with a plastic spatula and the cured thickness layer is measured. It was found that with visible light and an exposure duration of 20 seconds a cured layer thickness of 30 mm can be achieved, the surface hardness of the cured composition being 200 MPa.

In the curing through of a material drop it was found that the drop is completely cured after a few seconds and that the surface is absolutely dry, i.e. does not have any smeary layer.

The composition according to the invention is thus excellently suited to making coating lacquers for dental plasters, dentures and crown and bridge veneer materials. The composition, however, is likewise suited for applications such as the embedding, bonding, and coating of electric and electronic components, pieces and parts.

EXAMPLE 2:

(a) 12.2 parts by weight pentaerythrite tetramercaptoproprionate,
(b) 6.2 parts by weight triallyl triazine trione,
(c) 0.068 parts by weight bis-(2,6-dichlorobenzoyl)-4-N-propyl-phenyl phosphine oxide and
(d) 6.4 parts by weight 4,4'-bis-(acryloyloxyethyl oxyethoxy)-2,2-diphenyl propane, are stirred at room temperature to give a homogeneous mixture. The mixture has a viscosity of 0.7 Pa.s. The transparent solution thus obtained is introduced into a cylindrical mould of polyoxymethylene (diameter 5 mm, length 40 mm). The composition is exposed through the open end side of the cylindrical mould for 20 seconds with visible light of a wavelength of >400 nm by means of a commercially available dental radiator (Elipar-Vision/ESPE). To determine the curing depth or the thickness of the cured layer the soft or gellike components not polymerized remote from the irradiated surface are removed with a plastic spatula, and the cured thickness layer is measured. It was found that with visible light and an exposure duration of 20 seconds a cured layer thickness of 15 mm can be achieved, the surface hardness of the cured composition being 250 MPa.

In the curing through of a material drop it was found that the drop is completely cured after a few seconds and that the surface is absolutely dry, i.e. does not have any smeary layer. The composition according to the invention is thus excellently suited to making coating lacquers for dental plasters, dentures and crown and bridge veneer materials; likewise, it is excellently suited to performing embeddings, bondings, and coatings of electric and electronic components, pieces and parts.

EXAMPLE 3:

12 g of the reaction product of allyl chloride (2 Mol) with a diol (1 Mol) made from the copolymerization of equal parts by weight tetrahydrofuran and ethylene oxide with a mean molecular weight of about 6,000 are worked to a homogeneous clear solution with 1 part by weight trimethylol propane trimercaptoundecanoate, 0.03 parts by weight pyrocatechol and 0.13 parts by weight 2,4,6-trimethylbenzoyl diphenyl phosphine oxide. 40 parts by weight of the solution thus made are kneaded with 30 parts by weight silanized pyrogenic silicic acid with a specific surface area of 140 m$^2$/g to give a homogeneous thixotropic paste which is flowable under pressure but firm in the state of rest.

After an exposure lasting 40 seconds with visible light of a wavelength >400 nm using a commercially available dental radiator (Elipar-Visio/ESPE), a drop of this material is completely polymerized through and the polymer has a smooth absolutely dry surface without smeary layer. The resulting cured mass is rubber-elastic or elastomeric, has excellent elastic properties and is extremely resistant to tearing. To determine the Shore-A hardness according to DIN 53 505 a cylindrical specimen having a diameter of 2.5 cm and a height of 3.5. cm is made by 2-minute irradiating with the Elipar-Visio device. The Shore-A hardness is 52 and shows no further change after further irradiation.

A commercially available photocuring impression material ("Genesis", manufacturer: Caulk) on an acrylate basis, after the same exposure duration with the Elipar-Visio device, gives a moderately elastic tear-resistant rubber with a Shore-A hardness of 70. A shore-A hardness in the range of 50-60 is ideal for use as a dental impression composition, because only then is it ensured that on removal from the mouth of the patient there is no danger of damage to the tooth material and that when casting the impression with plaster and subsequent removal from the mould the plaster stumps do not break off. A cured drop of the commerically usual product (comparative material) has on all free surfaces a smeary layer which can be wiped off. Even after wiping off the smeary layer a tacky surface remains.

The composition according to the invention is thus excellently suited as dental impression composition.

We claim:

1. A photopolymerizable dental composition which is curable with visible light and which apart from the usual auxiliary substances and additives contains polymerizable monomers of the group of the poly-thiol compounds each having at leat two thiol groups and polymerizable monomers of the group of the poly-ene compounds each having at least two ethylenically unsaturated groups and at least one photoinitiator, wherein said composition contains respectively related to the sum of all the polymerizable monomers (a) at least 10% by weight of one or more of the poly-thiol compounds, (b) at least 10% by weight of one or more of the poly-ene compounds and (c) as photoinitiator 0.01-5% by weight of at least one acyl phosphine compound of the formula I

wherein $m=1$, $n=1$ and $x=0$ or
$m=2$, $n=0$ and $x=0$ or S, $R^1$ is a straight-chain or branched $C_{1-6}$-alkyl radical, a cyclohexyl, cyclopentyl, phenyl, naphthyl or biphenylyl radical, a cyclopentyl, cyclohexyl, phenyl, naphthyl or biphenylyl radical which is substituted by F, Cl, Br, I, $C_1$-$C_{12}$-alkyl and/or $C_1$-$C_{11}$-alkoxyl, an S or N-containing 5 or 6-member heterocylcic ring;

$R^2$ and $R^3$, which are identical or different, denote a cyclohexyl, cyclopentyl, phenyl, naphthyl or biphenylyl radical, a cyclopentyl, cyclohexyl, phenyl, naphthyl or biphenylyl radical which is substituted by F, Cl, Br, I, $C_1$-$C_{12}$-alkyl and/or $C_1$-$C_{11}$-alkoxyl, or an S or N-containing 5 or 6-member heterocyclic ring or $R^2$ and $R^3$ are linked together to form a ring which contains 4 to 10 carbon atoms and can be substituted by 1 to 6 $C_{1-4}$-alkyl radicals, and (d) 0 to 79.99% by weight with respect to the sum of all the polymerizable monomers, of an acrylic acid ester and/or methacrylic acid ester of an at least di-functional alcohol, said ester, when present, being at least 20% by weight.

2. The composition of claim 1, containing at least 20% by weight of the component (a) with respect to the sum of all the polymerizable monomers.

3. The composition of claim 1, wherein at least a third of the poly-thiol compounds of the component (a) is at least trifunctional.

4. The composition of claim 1, containing at least 20% by weight of the component (b) with respect to the sum of all the polymerizable monomers.

5. The composition of claim 1, wherein at least a third of the poly-ene compounds of the component (b) contains at least three ethylenically unsaturated groups.

6. The composition of claim 1, wherein the ethylenically unsaturated groups of the poly-ene compound(s) of the component (b) are substituted.

7. The composition of claim 1, wherein the ethylenically unsaturated groups of the poly-ene compound(s) of the component (b) are selected from the group consisting of the O-allyl, N-allyl, O-vinyl, N-vinyl and p-vinyl phenol ether groups.

8. The composition of claim 1, wherein the molar ratio between the ethylenically unsaturated groups of the compounds of the component (b) and the thiol groups of the compounds of the component (a) is from 0.2:1 to 5:1.

9. The composition of claim 8, wherein the molar ratio between said ethylenically unsaturated groups of the compounds of said component (b) and said thiol groups of the compounds of said component (a) is from 0.75:1 to 1.5:1.

10. The composition of claim 1, wherein the poly-thiol compound(s) of the component (a) and/or the poly-ene compound(s) of the component (b) have a polyether centre piece in their molecule.

11. The composition of claim 1, containing from 0.1 to 3% by weight of the component (c) with respect to the sum of all the polymerizable monomers.

12. The composition of claim 1, containing as photoinitiator 2,4,6-trimethylbenzoyl-diphenyl phosphine oxide or bis-(2,6-dichlorobenzoyl)-4'-n-propylphenyl phosphine oxide.

13. The composition of claim 1, containing as usual auxiliary substances and additives finely divided fillers in an amount of up to 90% by weight with respect to the total composition.

14. The composition of claim 13, containing silanized pyrogenic silicic acid as a filler.

15. The composition of claim 1, wherein component (d) comprises 40 to 60% by weight with respect to the sum of all the polymerizable monomers, of an acrylic acid ester and/or methacrylic acid ester of an at least difunctional alcohol.

* * * * *